United States Patent [19]

O'Leary et al.

[11] Patent Number: 4,798,590

[45] Date of Patent: Jan. 17, 1989

[54] INTRAVENOUS INFUSION PUMPING SYSTEM INCLUDING INDEPENDENT PUMP SET

[75] Inventors: William J. O'Leary, Huntington; Thomas J. Hartnett, Jr., Greenlawn, both of N.Y.; Richard G. Jones, Lebanon, N.J.

[73] Assignee: Medical Technology Products, Inc., Huntington, N.Y.

[21] Appl. No.: 554,617

[22] Filed: Nov. 22, 1983

[51] Int. Cl.$^4$ .............................................. A61M 5/00
[52] U.S. Cl. ..................................... 604/153; 417/477
[58] Field of Search .................... 604/30, 49, 151–153; 417/477

[56] References Cited

U.S. PATENT DOCUMENTS

| Re. 27,376 | 5/1972 | Pickup | 417/477 |
| 2,899,907 | 8/1959 | Becher | 417/477 |
| 3,832,096 | 8/1974 | Gelfand | 417/477 |
| 3,963,023 | 6/1976 | Hankinson | 417/477 |
| 4,210,138 | 7/1980 | Jess et al. | 417/477 X |
| 4,347,874 | 9/1982 | Sullivan et al. | 606/30 X |

Primary Examiner—Dalton L. Truluck
Attorney, Agent, or Firm—Michael Ebert

[57] ABSTRACT

An intravenous infusion pumping system in which an independent and therefore disposable pump set cooperates with a rotor assembly block to produce a peristaltic action conveying a therapeutic solution drawn from a container into a patient. The pump set, which includes a flow line extending between the container and the patient, has a pump chamber interposed therein constituted by a precisely-dimensioned, flexible tube terminating in inlet and outlet connectors. The tube is looped in a block cavity to conform to an arcuate stator wall therein and is subjected to compression by a pair of diametrically-opposed rollers carried by the rotor, the rollers pressing the tube against the wall to occlude the tube and thereby trap the fluid therein. As the rotor turns, the points of occlusion are advanced to propel the fluid toward the outlet. To assure a pumping action in the proper direction, the inlet connector is provided with a flange having a predetermined size which is seated in a matching slot in an inlet socket in the block, the outlet connector having a flange of different size seated in a matching slot in an outlet socket, thereby precluding reversal of the pump chamber. To prevent air embolism, the transparent outlet connector is associated with a light beam detector that senses the presence of air in the flow therethrough to generate a signal which deactivates the pump.

6 Claims, 3 Drawing Sheets

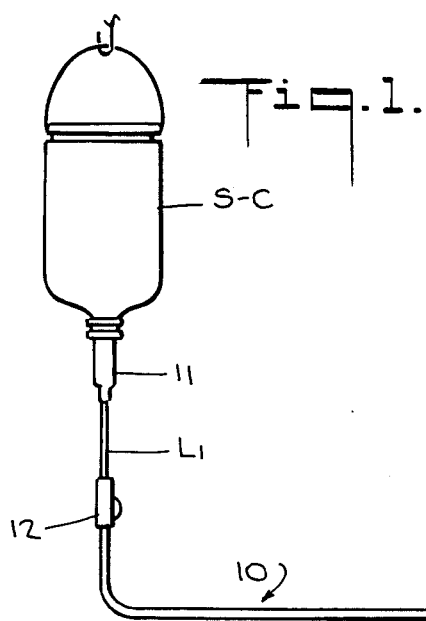
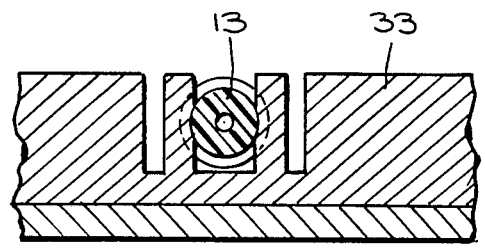
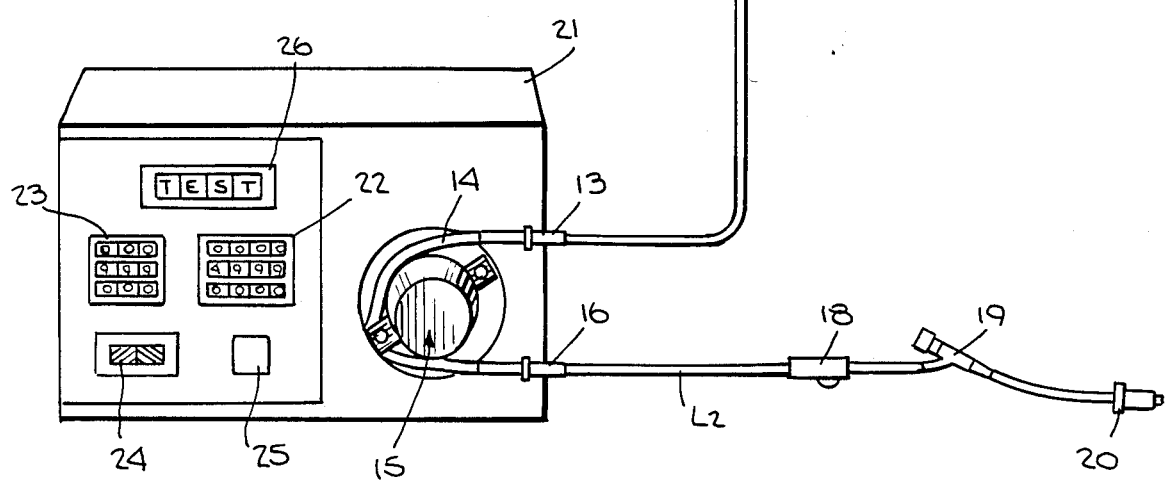
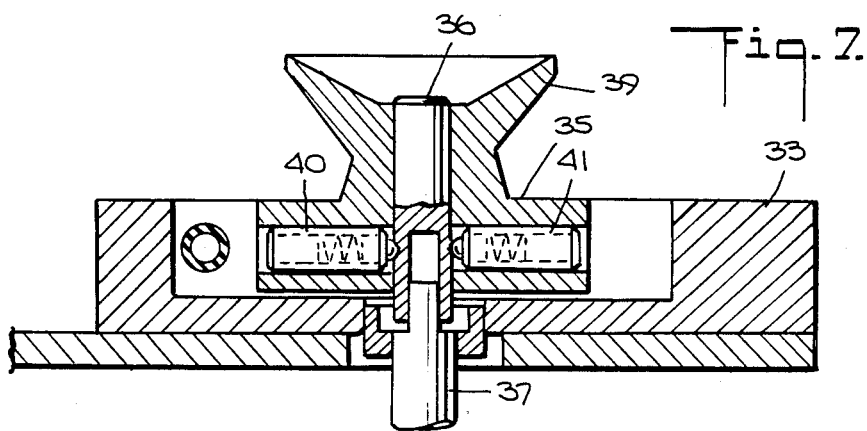

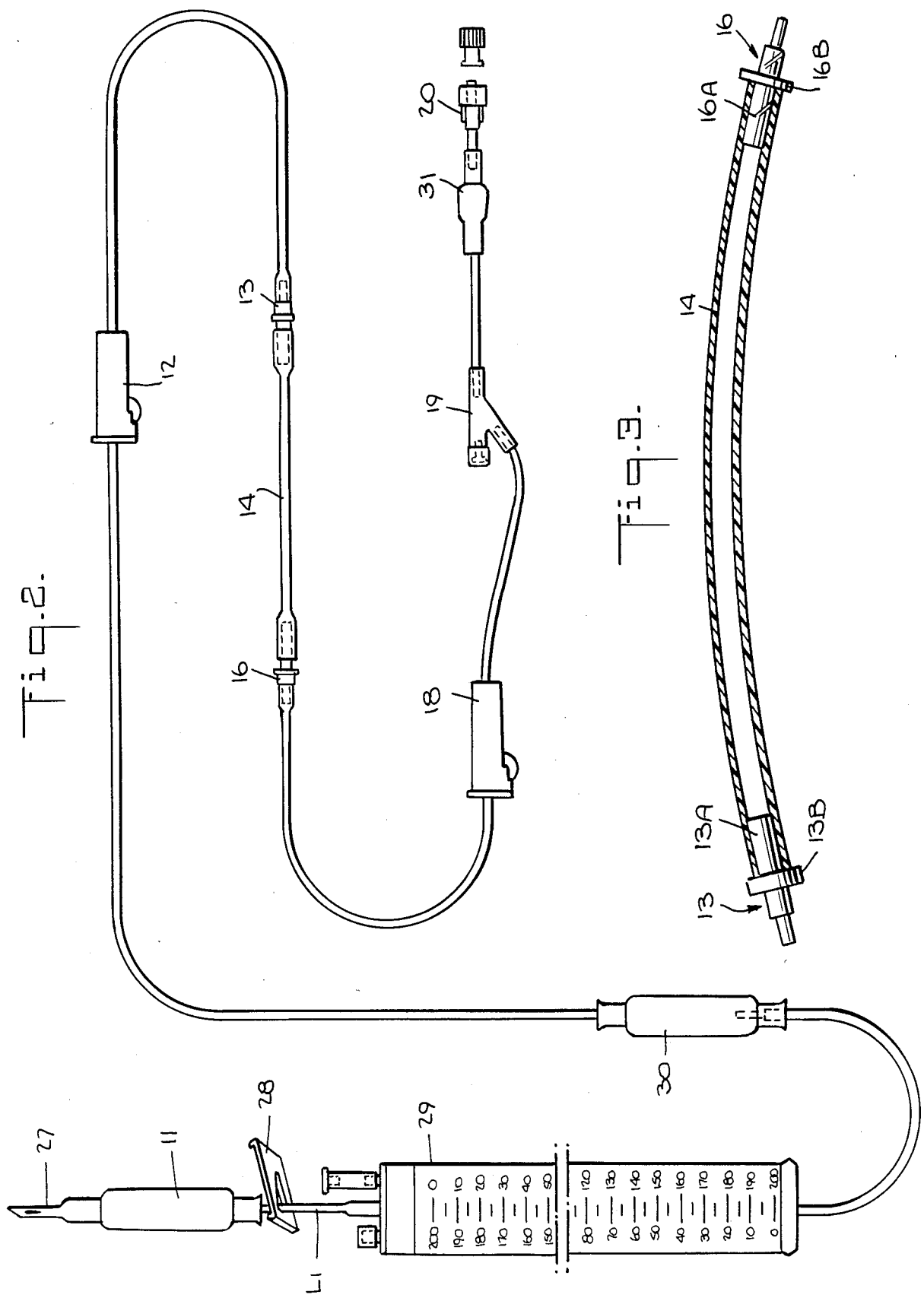

INTRAVENOUS INFUSION PUMPING SYSTEM INCLUDING INDEPENDENT PUMP SET

BACKGROUND OF INVENTION

1. Field of Invention

This invention relates generally to infusion pumping systems for medical use in intravenous therapy, and more particularly to a disposable pump set adapted to cooperate with a rotor assembly block to provide a peristaltic pump action.

In modern medical practice, patients in hospitals and in other facilities are in many cases treated for various maladies with medicaments and nutritional substances dissolved in a liquid carrier. These therapeutic solutions are infused directly into a vein or artery of the patient by a process generally designated as intravenous (IV) therapy.

The simplest embodiment of an IV infusion system takes the form of a solution container supported at an elevated position relative to the patient to be treated to provide gravity flow through a flexible pipe leading to a catheter inserted in the patient. The rate of fluid flow is set by an adjustable clamp in the fluid line, flow rate being indicated by a drip chamber just below the container. By counting the number of drops which fall during a given interval, the attendant obtains an approximate reading of flow rate.

A gravity feed IV system leaves much to be desired; for while the physician treating the patient will specify a particular solution for IV therapy and indicate the volume of solution to be administered, as well as the flow rate of infusion, it is difficult for the nurse to comply with this prescription unless she carefully monitors the gravity-feed system to be sure it is operating in the desired manner. Since a nurse has other pressing duties, she may not be able to give the system the repeated attention it demands.

To obviate the drawbacks incident to gravity-feed IV systems, it is known to employ electronically-controlled, motor-operated peristaltic pumps to feed a prescribed volume of IV solution into a patient at a carefully regulated flow rate. The clinical use of such infusion pumps is now commonplace in intensive care and special care hospital facilities for patients who require IV infusion with a degree of accuracy and reliability that cannot be realized with a gravity feed system.

When using an IV pumping system, one must exercise care to minimize the risk of air embolism. Thus, should the pump still be in operation after the container is emptied of its solution, the pump will then proceed to infuse air into the patient, and this may have serious consequences. Moreover, air, rather than solution, may be pumped into the patient should the peristaltic pump chamber included in the pump set be ruptured or separated from its fittings.

One commercially available IV infusion pump system is the "Extracorporeal" Model 2100 infusion pump manufactured by Extracorporeal Medical Specialties, Inc., of King of Prussia, Pa. The main component of this system is a solid state motordriven device for controlling the rate of flow during the administration of IV fluids. The device makes use of a rotarytype pumping action employing a single size pump chamber for all flow rates.

In the Extracorporeal system, the pumping action is effected by means of a detachable plastic rotor assembly and an independent IV pump set having integral therewith a silicon-rubber tube function as the pump chamber. This pump chamber is joined to the rotor assembly which is provided with a set of rollers, pressure between the rollers and the stator wall of the assembly acting to occlude the flexible pump chamber and thereby trap the fluid therein.

As the rotor is turned by the internal motor, the points of occlusion then advance to progressively push the fluid through the pump chamber, flow rate being controlled by adjusting the speed of the motor. Because the IV pump set is independent of the rotor assembly, it affords a sealed, sterile fluid pathway. The set is disposable after a single 24-hour use in compliance with existing medical requirements.

Another commercially-available IV system is the "Simplicity" volumetric infusion pump system manufactured by Critikon, Inc., of Tampa, Fla. The "Simplicity" system, which is generally similar in structure and function to the system marketed by Extracorporeal, also includes an independent pump set having a flexible pump chamber which cooperates with a rotor assembly to define a peristaltic pump for forcing a therapeutic fluid into the patient at a controlled rate. It further includes an alarm that is activated if the fluid container is empty, or if the tubing in the set is kinked or is dislodged from the rotor assembly.

In the "Simplicity" system, an empty bottle condition is sensed by a flow detector placed in the upper portion of the drip chamber so that it will detect the absence of fluid from the bottle while there is still fluid in the line. But no protective means are provided in this or any other commercially-available system for sensing the presence of air in the line at the outlet side of the pump chamber leading to the patient.

Thus, in practice, air may be drawn into the relatively delicate pump chamber if it is torn or punctured, or separated from its fittings. A flow detector which senses air resulting from the absence of fluid flow from the container will not give an alarm should air be entrained into the pump chamber from which it will be pumped into the patient and give rise to air embolism.

Another source of danger in an IV infusion pumping system lies in the possibility that the independent pump set which cooperates with the rotor assembly may inadvertently be installed therein in reverse; that is to say, with its outlet connector placed on the inlet side and its inlet connector placed on the outlet side of the rotor assembly. In this event, instead of infusing a therapeutic solution into the patient, blood will be drawn out of the patient. No provision is made in systems of the type heretofore known to positively preclude this possibility, which is sometimes referred to as a "Vampire" action.

Another problem heretofore experienced with systems which make use of an independent pump set is the difficulty of joining the set to the rotor assembly. While experienced personnel may be able to correctly install the set, this is not true of the more typical hospital attendant.

2. Prior Art

Systems which include motor-controlled pumps in an IV system to feed a solution intravenously in a patient are disclosed in the following patents:

| | | |
|---|---|---|
| Moulinier | 2,483,924 | 1949 |
| Ferrara et al. | 2,102,523 | 1937 |
| Lee | 2,804,023 | 1957 |
| Daniels | 2,909,125 | 1959 |

| -continued | | |
|---|---|---|
| Cantor | 3,138,104 | 1964 |
| Hahn | 3,137,242 | 1964 |

Among the patents which disclose electronic control equipment to govern the operation of the pump motor in an IV system are the following:

| Jess et al. | 4,217,993 | 1980 |
|---|---|---|
| Willock | 3,848,592 | 1974 |
| Weishaar | 3,799,702 | 1974 |
| Shim | 4,278,085 | 1981 |
| Brown | 4,256,437 | 1981 |

The following patents relate tot he structure of peristaltic pumps;

| Lepp et al. | 4,142,845 | 1979 |
|---|---|---|
| Casson et al. | 4,184,815 | 1980 |
| Spinosa et al. | 3,927,955 | 1975 |
| Hankinson | 3,963,023 | 1976 |

SUMMARY OF INVENTION

In view of the foregoing, the main object of this invention is to provide in an intravenous volumetric infusion system an independent and therefore disposable pump set that is adapted to cooperate with a rotor assembly block to produce a peristaltic action feeding a therapeutic solution drawn from a container into a patient, the pump set being readily attachable to and removable from the block to facilitate the operation of the system by relatively unskilled personnel.

More particularly, an object of this invention is to provide a pump set in which the flow line extending between the solution container and the patient has a pump chamber interposed therein constituted by a flexible tube terminating in inlet and outlet connectors, the tube having predetermined inner and outer diameters and a fixed length, whereby a precise volume of solution is held therein between the two connectors, this volume being delivered to the patient during each revolution of the rotor.

A significant feature of a system in accordance with the invention is that the total volume infused and the rate of infusion may be precisely governed so that the solution may be administered in compliance with the physician's prescription.

Also an object of the invention is to provide a rotor assembly block in which the rotor slips on the square shaft of a motor and includes a handle whereby the pump chamber may be manually installed without difficulty on the block to be engaged by pressure rollers carried by the rotor, or disengaged therefrom for disposal after use.

Still another object of this invention is to provide a pump set whose inlet and outlet connectors can only be seated in complementary inlet and outlet sockets on the rotor assembly block whereby fluid flow in the reverse direction is precluded.

Yet another object of this invention is to provide a pump set having a transparent outlet connector which is associated with a light beam detector adapted to sense the presence of air in the fluid flow and generate a signal arresting the pump action to prevent air embolism.

Briefly stated, these objects are attained in an intravenous infusion pumping system in which an independent and therefore disposable pump set cooperates with a rotor assembly block to produce a peristalatic action conveying a therapeutic solution drawn from a container into a patient. The pump set, which includes a flow line extending between the container and the patient, has a pump chamber interposed therein constituted by a precisely-dimensioned, flexible tube terminating in inlet and outlet connectors. The tube is looped in a block cavity to conform to an arcuate stator wall therein and is subjected to compression by a pair of diametrically-opposed rollers carried by the rotor, the rollers pressing the tube against the wall to occlude the tube and thereby trap the fluid therein. As the rotor turns, the points of occlusion are advanced to propel the fluid toward the outlet. To assure a pumping action in the proper direction, the inlet connector is provided with a flange having a predetermined size which is seated in a matching slot in an inlet socket in the block, the outlet connector having a flange of different size seated in a matching slot in an inlet socket in the block, the outlet connector having a flange of different size seated in a matching slot in an outlet socket, thereby precluding reversal of the pump chamber. To prevent air embolism, the transparent outlet connector is associated with a light beam detector that senses the presence of air in the flow therethrough to generate a signal which de-activates the pump.

OUTLINE OF DRAWINGS

For a better understanding of the invention as well as other objects and further features thereof, reference is made to the following detailed description to be read in conjunction with the accompanying drawings, wherein:

FIG. 1 illustrates an intravenous volumetric infusion pumping system which includes a pump set and a rotor assembly block in accordance with the invention;

FIG. 2 is a separate and more detailed showing of the pump set;

FIG. 3 is a perspective view of the pump chamber included in the pump set;

FIG. 6 is a section taken in the plane indicated by line 6—6 in FIG. 4; and

FIG. 7 is a section taken in the plane indicated by line 7—7 in FIG. 4.

DESCRIPTION OF INVENTION

The IV System

Figure 4:
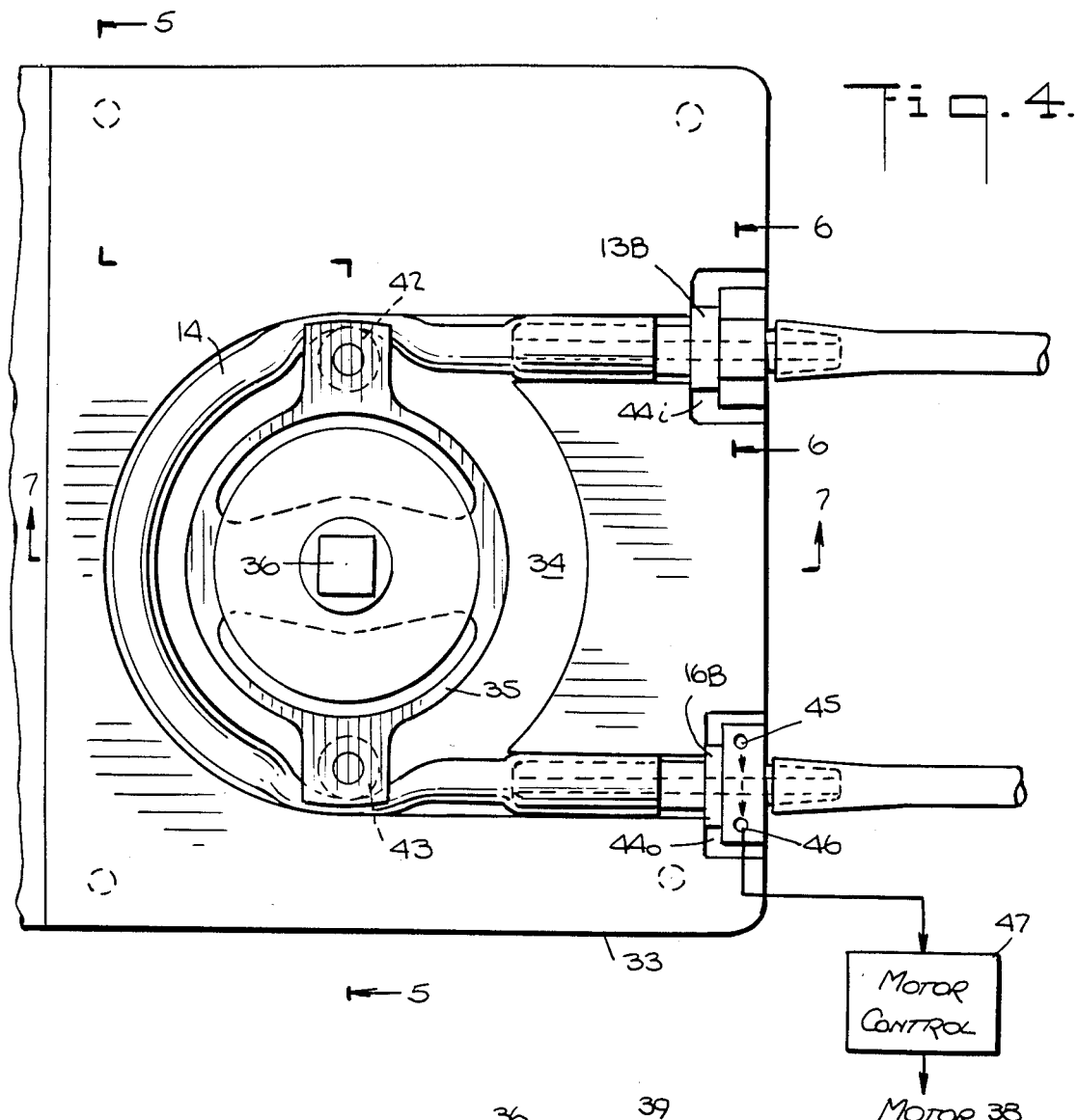
FIG. 4 is a plan view of the rotor assembly block.

Referring now to FIG. 1, there is shown a volumetric IV infusion pumping system in accordance with the invention, the system including an independent pump set, generally designated by numeral 10, which is shown in highly simplified form. This set is provided with a drip chamber 11 which receives fluid from a solution container S-C suspended from a suitable stand.

Fluid from drip chamber 11 is conducted by a flexible plastic line $L_1$ having a roller clamp 12 thereon to an inlet connector 13 coupled to one end of a pump chamber preferably formed by a silicone-rubber tube 14. The other end of the pump chamber is coupled to an outlet connector 16, as shown separately in FIG. 3.

The silicone-rubber chamber has exact dimensions for its length, and its inner and outer diameters as well as durometer and elasticity. As a consequence, there is a precise volume of solution in the chamber between the inlet and outlet connectors which is delivered by the rotary compression action of a rotor assembly, generally designated by numeral 15. The outlet connector 16 of pump chamber 14 is coupled through line $L_2$ having a roller clamp 18 and a Y-site 19 therein to a luer 20. This is attachable to a catheter (not shown) inserted in a vein or artery of the patient.

Housed within a compact casing 21 is the internal motor for turning the rotor of the rotor assembly 15 at a desired rate, and an electronic motor control network which is settable to control the total volume of fluid to be infused and the rate of infusion. This motor control network forms no part of the present invention; and while its arrangement will now be described in general terms, it is to be understood that the rotor may be driven by a motor whose operation is governed by any known means adapted to adjust the total volume of fluid to be infused and its control rate.

On the front panel of the casing is a three-digit rotary switch 22 which is settable to control the total amount of volume to be infused into the patient. This switch is of the rotary push button type that affords 1 to 999 milliliters total volume. It has a row of buttons below the three digits and a row thereabove that allows the operator to step in either ascending or descending digital values to obtain the desired value of total volume.

Adjacent switch 22 on the front panel is a four-digit rotary switch 23 which functions in the same manner as switch 22 and acts to control the pump's flow rate in milliliters per hour. The flow rate ranges from 0.1 to 499.9 milliliters per hour.

Also provided is an on/off rocker switch 24 for power control, and a start/stop momentary push button switch 25. The circuit arrangement is such that when power switch 24 is "on," the start/stop switch 25 must then be depressed in order to initiate the functions of the infusion pump.

Included in the electronic motor control network is a microcomputer, access thereto being obtained by depressing start-stop switch 25. This action enters into the memory of the computers the values selected by adjustment of rotary switches 22 and 23 for total volume and flow rate, and it starts the pump motor.

Initial depression of the start-stop momentary switch 25 locks the selected values into the computer memory and locks out any later attempted changes in the selected values. Thus, while the pump is in its operating mode, operation of the two panel switches which control total volume to be infused and the infusion rate cannot alter the operation of the pump at that time. To change the values of these two switches, the on/off power switch (24) must be turned "off" and then "on" in a manner similar to the clear button on a calculator.

Start/stop switch 25, when operated, will bring pump infusion to a halt to allow the operator to make any adjustments with the associated disposable part of the system. Pressing this switch a second time will re-start infusion without altering the values then held in the microcomputer. In the event of an alarm situation, the infusion pump is caused automatically to stop and to be placed into an alarm mode to produce an audible alarm signal. By pressing the start-stop momentary contact switch 25 once, this action will cut off the audible alarm, but it will not clear a LED diagnostic alpha-numeric readout 26 on the front panel. A second pressing of this switch will initiate the resumption of the infusion mode from where it left off from the alarm condition.

The specific functions of the infusion pump are displayed on the alpha-numerical LED display 26. This display consists of four characters, each character having fourteen segments to selectively produce letters or numbers. The LED display also has four decimal points.

When power is first turned on, this is referred to as a power-up mode. In the initial power-up mode, the pump will perform a diagnostic test. The LED screen will then display "Test." If the self-diagnostics check out, the LED screen will then present the letters "OK." If there are any faults in the pump's system, the LED screen will display "ERR" to designate error. The LED screen will then indicate the problem area. The problem area may either be the internal (pump) or the external (infusion pump set) sensing systems. The LED screen will display either "INT" or "EXT" so that the operator will know whether there is a problem with the internal part of the pump or whether it is the infusion pump set being integrated with the pump that is in error. The LED presentation also provides a constant display of the amount of solution being infused. Also shown on this screen are alarm conditions, such as a low battery power condition, or malfunctions such as a drip rate which is less than that required or a condition in which the torque of the pump motor is below par.

The Pump Set

FIG. 2 illustrates a preferred embodiment of the pump set 10 in greater detail. In order to penetrate the stopper of the solution container, the pump set is provided with a universal hollow spike 27 just above drip chamber 11. The line $L_1$ leading from drip chamber 11, is provided with a slide clamp 28, the line then entering a burette chamber 29 having a graduated scale.

From burette chamber 29, the fluid flows into a microdrip chamber 30, and from there the line is connected through roller clamp 12 to the inlet connector 13 of pump chamber 14 whose outlet connector 16 is coupled through roller clamp 18 and Y-site 19 to a flash bulb 31 coupled to the male luer 20 which is provided with a removable guard.

The pump set need not be of the type described and may exclude, for example, the burette 29 and the microdrip chamber 30; but in a pump set in accordance with the invention, it must have incorporated therein a pump chamber 14 having inlet and outlet connectors 13 and 16 of the type shown.

Each of these connectors includes, as shown in FIG. 3, a stem (13A & 16A) to receive the ends of the pump chamber tube 14 and a flange (13B and 16B). It is important to note that while both flanges have the same diameter, the inlet flange 13B is substantially thicker than outlet flange 16B. It is important to note that inlet connector 13 is formed of opaque plastic material, whereas outlet connector 16 is fabricated of transparent material. The reasons for these distinctions will be later explained.

The Rotor Assembly Block

Figure 5:
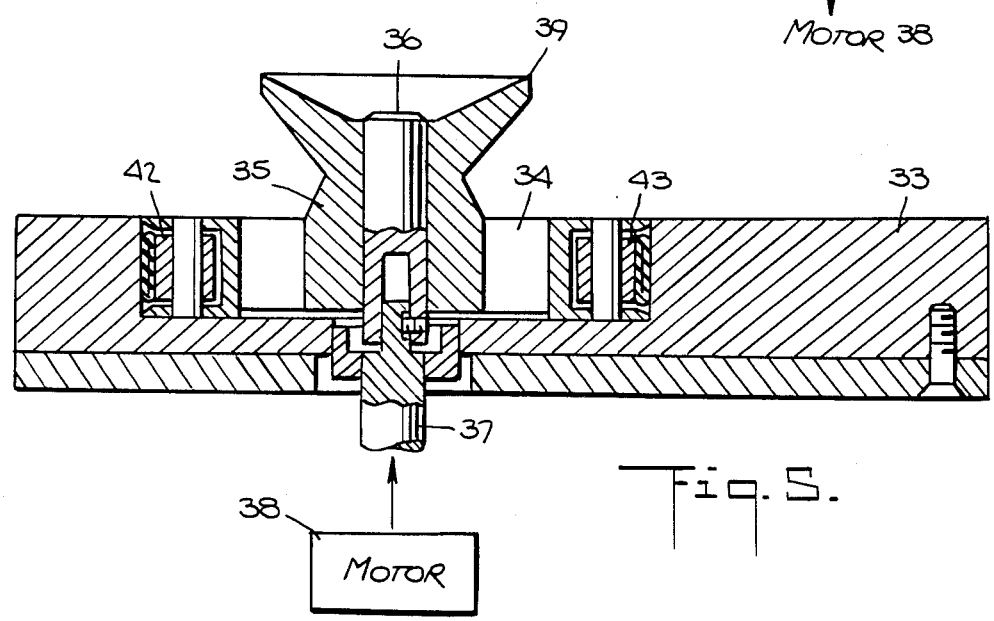
FIG. 5 is a section taken in the plane indicated by line 5—5 in FIG. 4.

As shown in FIGS. 4 to 7, this unit includes a rectangular block 33 fabricated of synthetic plastic material having a circular cavity 34 therein which communicates with parallel inlet and outlet channels. Seated coaxially within the cavity is a circular rotor 35 having a square center hole to accommodate a square motor shaft extension 36. This is keyed to the motor shaft 37 of a stepping motor 38. The motor is energized by periodic pulses yielded by the electronic control network at a regulated rate which determines the stepping speed of the motor.

Protruding upwardly from rotor 35 and integral therewith is a cone-shaped knob 39 having a concave face to facilitate manual withdrawal of the rotor from the shaft extension and the rotor assembly block. This knob also affords rotary leverage to facilitate turning the rotor when installing pump chamber 14 on the rotor assembly block so that it is engaged by pressure rollers.

The shaft extension 36 which passes through the center of knob 39 protrudes slightly above the concave face thereof. This protuberance provides a fulcrum for pressing the thumb against the shaft extension when pulling the rotor unit off the block. Shaft extension 36 is provided on all four sides with small indentations which nest spring-loaded detents, two of which, 40 and 41, are shown in FIG. 7. Thus, when the rotor unit is slipped over shaft extension 36, the detents lock it in place; and when the rotor unit is withdrawn from the shaft extension, one must overcome the action of the spring-loaded detents.

Rotor 35 is provided at diametrically-opposed positions with arms carrying a pair of load-bearing rollers 42 and 43 that engage the flexible tube of pump chamber 14, which tube is looped within cavity 34 against an arcuate wall thereof. The inlet connector 13 of the pump chamber is seated within an inlet channel socket in the block having a slot 44$_i$ therein which matches the width of flange 13B. The outlet connector 15 of the pump chamber is seated within an outlet channel socket in the block having a slot 44$_o$ therein which matches flange 16B. Since flange 13B is thicker than flange 16B, the inlet connector cannot be seated within the outlet socket, and reversal of flow is thereby precluded.

Rollers 42 and 43 provide occlusive pressure against the silicon-rubber tube which defines pump chamber 14; and while these rollers ride along the tube and press it against the arcuate side wall of the cavity to produce a peristaltic pump action, the rollers do not stretch the tube but act only to create the moving compressive force to propel the fluid therein from the inlet to the outlet. This produces a negative pressure at the inlet side serving to draw liquid from the solution container, the liquid ejected from the outlet being delivered to the patient.

Inlet connector 13 is opaque and may be colored, thereby distinctly marking this as the inlet connector so that the operator will, as a matter of course, always insert this connect of in the inlet channel socket on the block.

Outlet connector 16 is transparent, thereby making it possible to distinguish between liquid and air flow therethrough by means of a light beam detector. This is constituted by an LED light source 45 disposed on one side of the clear connector, and a phototransistor 46 disposed on the opposite side.

The resultant light beam which traverses the inlet connector is sufficiently attenuated when liquid is interposed between the light source and the transistor so that little signal is then yielded by transistor 46. But if the flow of liquid is interrupted by an air bubble, the beam strength is then such as to produce a transistor signal which rises above a predetermined threshold level. This signal is applied to a motor control circuit 47 to arrest the operation of motor 38 and thereby prevent air embolism.

Thus, the arrangement is such that the rotor in the assembly block is easily manipulated by an operator when installing the pump set or when removing the set for disposal, reversal of the pump set relative to the rotor assembly being precluded and air embolism being prevented.

While there has been shown and described a preferred embodiment of an intravenous infusion pumping system including independent pump set in accordance with the invention, it will be appreciated that many changes and modifications may be made therein without, however, departing from the essential spirit thereof.

We claim:

1. An intravenous infusion system for supplying a therapeutic solution from a container therefor to a patient, said system comprising:
   A. an independent pump set having a flow line extending from the container to the patient, said line having interposed therein a pump chamber constituted by a flexible tube terminating in an inlet connector and a transparent outlet connector each having a circular flange, the inlet connector flange being thicker than the outlet flange;
   B. a rotor assembly block having a circular cavity within which is seated a rotor carrying a pair of diametrically-opposed rollers, the tube being looped in the cavity against an arcuate stator wall thereof, the flange of the inlet connector being seated in a matching slot of an inlet channel socket in the block leading to the cavity, and the flange of the outlet connector being seated in a matching slot of a parallel outlet channel socket in the block leading to the cavity which is dimensioned to accept only the outlet connector, thereby precluding reversal of the pump chamber, the rollers pressing the tube against the wall to occlude the tube and thereby trap the fluid therein;
   C. a motor driving the rotor, whereby as the rotor turns, the points of occlusion are advanced to propel the fluid toward the outlet connector;
   D. a light beam detector constituted by a light beam source disposed on one side of the transparent outlet connector to project a light beam therethrough and a photo sensor disposed on the opposite side of the outlet connector to intercept said beam to produce a control signal only when air passes through the outlet connector; and
   E. a motor control circuit coupled to said motor and responsive to said signal to arrest said motor to prevent air embolism.

2. A system as set forth in claim 1, wherein said pump set includes a spike at one end of the line to penetrate the stopper of the container, and a male luer at the other end to be coupled to a catheter for insertion in a vein or artery of the patient.

3. A system as set forth in claim 1, wherein said tube is of silicone-rubber and is precisely dimensioned to hold a predetermined volume of the fluid.

4. A system as set forth in claim 1, wherein said motor is provided with a square shaft extension, and said rotor has a matching square center hole so that said rotor may readily be slipped on and off said extension, said rotor being provided with spring-loaded detent means which cooperate with indentations in said shaft extension to lock said rotor to said extension.

5. A system as set forth in claim 4, wherein said rotor is provided with a protruding knob to facilitate its insertion on or removal from the shaft extension, and to facilitate manual turning of the rotor.

6. A system as set forth in claim 5, wherein said square shaft extension protrudes slightly above the knob to provide a fulcrum for the thumb of the operator.

* * * * *